United States Patent [19]
Madsen et al.

[11] Patent Number: 5,741,662
[45] Date of Patent: Apr. 21, 1998

[54] DIRECT STAIN SPECIFIC BINDING ASSAYS FOR MICROORGANISMS

[75] Inventors: Randall D. Madsen; Lorraine S. Bautista, both of San Diego; Jan W. Pawlak, Encinitas; Allan D. Pronovost, San Diego, all of Calif.

[73] Assignee: Quidel Corporation, San Diego, Calif.

[21] Appl. No.: 573,706

[22] Filed: Dec. 18, 1995

[51] Int. Cl.$^6$ .................... C12Q 1/04; C12Q 1/06; G01N 33/53; C12N 1/00

[52] U.S. Cl. .................... 435/34; 435/39; 435/36; 435/4; 435/882; 435/883; 435/884; 435/885; 435/921; 435/922; 435/923; 435/924; 435/947; 435/971; 435/975; 435/7.1; 544/347; 549/223; 549/227; 546/102

[58] Field of Search .................... 435/34, 39, 36, 435/4, 882, 883, 884, 885, 921, 922, 923, 924, 947, 971, 975, 7.1; 544/347; 549/223, 227; 546/102

[56] References Cited

U.S. PATENT DOCUMENTS

| | | | |
|---|---|---|---|
| 3,996,345 | 12/1976 | Ullman et al. | 435/4 |
| 4,829,005 | 5/1989 | Friedman et al. | 435/4 |
| 4,943,522 | 7/1990 | Eisinger et al. | 435/4 |
| 5,372,935 | 12/1994 | Capps | 435/34 |
| 5,424,193 | 6/1995 | Pronovost et al. | 435/7.32 |

FOREIGN PATENT DOCUMENTS

| | | |
|---|---|---|
| 0 074520 | 3/1983 | European Pat. Off. . |
| 1 194256 | 6/1970 | United Kingdom . |
| 9212428 | 7/1992 | WIPO . |

OTHER PUBLICATIONS

Valentin–Weigand et al, Microbiol. Immunol., vol. 31(10), pp. 1017–1023, 1987. Month not available.

*Primary Examiner*—Louise Leary
*Attorney, Agent, or Firm*—Townsend and Townsend and Crew LLP

[57] ABSTRACT

The present invention provides specific binding solid phase assay methods and kits for the detection of the presence or absence of a microorganism by directly staining the microorganism and specifically capturing the stained microorganism on a solid support. The methods find particular utility in the detection of Candida. The methods may simultaneously detect the presence or absence of multiple microorganisms.

38 Claims, 1 Drawing Sheet

DIRECT STAIN SPECIFIC BINDING ASSAYS FOR MICROORGANISMS

BACKGROUND OF THE INVENTION

1. Field of the Invention

The present invention relates to methods, devices and kits for detecting analytes in a sample suspected of containing such an analyte. More particularly, the present invention relates to solid phase specific binding assays in which microorganisms can be detected by direct staining of the microorganism.

The detection of microbial pathogens in biological samples is of particular value in clinical medicine. As treatment may vary considerably depending upon the causative organism, accurate and rapid identification of pathogens in biological samples of patients suspected of having an infectious disease can be critical to provide prompt and appropriate treatment to patients. For example, many species of Streptococcus are pathogenic, causing both pyrogenic and hemolytic symptoms, and are common causes of infection of the respiratory tract, leading to sore throats, as well as more serious infections such as scarlet fever (*S. pyogenes*). *S. pneumoniae* is the principal cause of bacterial pneumonia. Most bacterial and fungal infections are treatable with appropriate antibiotics and antifungal agents. However, since a range of microorganisms may be responsible for the same symptoms in an infected individual, accurate diagnosis is critical for proper patient care as different pathogens may require different treatment regimens.

Recently, the widespread use of antibiotics and immunosuppressive therapies have led to a pronounced increase in the prevalence of fungal pathogens. Fungi typically lack peptidoglycan constituents in their cell wall and thus are not susceptible to the traditional forms of antibiotic therapy. As a result, the selective population pressure caused by antibiotic administration eliminates bacteria and may enable the rapid expansion and colonization by pathogenic fungi that are unaffected by the chosen regimen of antibiotic therapy. For example, candidiasis, caused by the fungal pathogens *Candida albicans* and *Candida tropicalis* is estimated to be the fourth largest source of blood borne infection and one of the most common forms of hospital-acquired infections. Another common fungal pathogen, *Aspergillus fumigatus*, causes aspergillosis, commonly characterized by lung infection. Therefore, rapid identification of disease-causing organisms, particularly fungal pathogens, in biological samples is important for a variety of disease-causing agents to direct appropriate therapy.

Microorganism-originated infections are not limited to the hospital setting. Fungal contamination is found in foods, soils and water. For example, apples and peanuts may contain lethal mycotoxins produced by fungal contaminants, such as, for example, the aflatoxins produced by *Aspergillus flavus*. Milk contamination by Salmonella or the hemolytic streptococci is a recurring problem in the dairy industry. Soil samples and water supplies may contain coliform bacteria such as *E. coli* and *Enterobacter aerogenes*, each of which can be life-threatening under certain circumstances. Therefore, rapid, simple and cost-effective methods are needed for detecting the presence of microbial pathogens in foods, water and soils.

Traditional methods involve culturing the microorganism followed by subsequent identification, typically by substrate and nutrient assays. Typically, the substrate and nutrient consumption tests such as the API, Enterotube and Micro-ID test require pure cultures for accurate results. Furthermore, culturing microbial pathogens usually requires at least 24 hours to produce a clinically usable specimen. More rapid methods of diagnosing microbial infections have been developed to provide timely results for guiding clinical therapy. Some of the most effective of these have been methods which employ immunological means to detect the microorganism.

The use of chromophoric and fluorescent dyes as "labels" in biological assay procedures is known. Typical assay protocols call for direct or indirect binding of a dye label to an analyte or analyte analog in a biological sample, wherein the presence or absence of the dye at a particular stage of the assay can be determined visually or spectrophotometrically and related to the amount of analyte present in the sample. A wide variety of specific assay protocols exist.

The use of dyes for staining biological materials, such as proteins, carbohydrates, nucleic acids and whole organisms is documented in the literature. It is known that certain dyes stain particular materials preferentially based on compatible chemistries of dye and ligand, such as, for example, Coomassie Blue and Methylene Blue for proteins, periodic acid-Schiff's reagent for carbohydrates, Crystal Violet, Safranin O and Trypan Blue for whole cell stains, ethidium bromide and Acridine Orange for nucleic acid staining and fluorescent stains such as rhodamine and Calcofluor White for detection by fluorescent microscopy.

Common methods of labelling microorganisms with dyes include systems in which a dyed particle, such as a dye-impregnated synthetic microsphere or liposome, conjugated to an antigen recognizing substance, such as an antibody, binds to the antigen on the microorganism, thus labelling the microorganism. Alternatively, enzyme labels which bind to the microorganism by immunologically mediated methods may be used. The labelled microorganism is subsequently detected by its binding to an immobilized capture antibody to produce an accumulation of a microorganism-antibody-dyed particle complex which can be visually detected. The location of two antibodies, one on the detector reagent, e.g., dyed latex microspheres, and the second on the capture zone on the solid phase, in a double antibody sandwich type assay can sometimes result in false positive signals, especially when the two antibodies are the same or from the same species.

While generally useful, methods for preparing particle-labelled microorganisms can be relatively complex, usually requiring multi-stage operations including preparation of the particle, coloring of the particle, attachment of the particle to the antibody, and blocking of the particle for use in immunoassays and subsequently binding the particle to the microorganism. Some particles, such as liposomes, are relatively unstable and do not provide uniform characteristics following storage or during use in some samples. Moreover, a loss of antibody binding capacity can often result from the particle attachment. Sometimes these particles are not compatible with the antibodies selected for a particular application. Enzyme labels have similar problems, such as enzyme instability and the need to bind the enzyme to the microorganism. In addition, enzyme labels usually require an additional step or reagent in which an enzyme substrate is provided to generate a detectable signal.

It would be desirable to provide improved labelling methods which do not require immunologically mediated binding of the label to the microorganism and do not suffer from the instability associated with particulate or enzymatic labels. Ideally, the method should be simple, direct and not interfere with the antigenicity and immunoreactivity of the microorganism. This invention provides such a method.

3

2. Summary of Related Art

U.S. Pat. No. 5,372,935 describes the use of Janus Green B to stain Candida.

U.S. Pat. No. 5,424,193 discloses the use of dyed microorganisms as labels in immunoassays. European Patent Application 0 074 520 discloses the use of stained Staphylococcus aureus coated with anti-HCG antibody. GB 1,194,256 discloses the use of stained E. coli, stained Brucella and stained yeast cells coupled to an antigenic substance such as human CGTH.

SUMMARY OF THE INVENTION

This invention provides assays, devices and kits for determining the presence or absence of a targeted microorganism in a fluid sample suspected of containing such a microorganism. The assay comprises:

a) combining the sample with a labelling reagent comprising a dye which directly stains the microorganism or a component thereof to provide a stained sample comprising a stained microorganism, b) optionally combining the stained sample with a reagent which adjusts the pH of the sample to a physiological pH to provide a neutralized sample, c) contacting the stained or neutralized sample with a matrix defining a flow path from a sample receiving zone to a capture zone located downstream from the sample receiving zone, wherein the capture zone comprises an immobilized specific binding pair member for the microorganism, c) observing the accumulation of the stained microorganism within the capture zone as a result of the stained microorganism flowing into and being immobilized within the capture zone by the specific binding pair member, and d) relating the accumulation of stained microorganism within the capture zone to the presence or absence of the microorganism in the fluid sample.

The invention also provides methods of detecting and specifically identifying the presence or absence of at least one of a plurality of microorganisms present in a sample by separately capturing each stained microorganism on a separate capture zone each containing a different specific binding pair member each being complementary to a different microorganism. Another aspect of the invention is the detection of the presence of any one of a plurality of microorganisms by immobilizing on a single capture zone an antibody or antibody mixture that binds to all of the targeted microorganisms.

The invention also provides an improvement in the detection of microorganisms by capture of a labelled microorganism on a solid support, wherein the improvement comprises directly staining the microorganism with a dye reagent and adjusting the pH of the sample to a physiological pH prior to capturing the stained microorganism on the solid support.

Another aspect of the invention are kits for detecting the presence of a microorganism in a fluid sample comprising in packaged combination a dye reagent capable of directly staining the microorganism and a matrix defining a flow path from a sample receiving zone to a capture zone located downstream from the sample receiving zone, wherein the capture zone comprises an immobilized specific binding pair member for the microorganism.

The invention finds particular utility in detecting Candida and Streptococcus. Preferably, the invention uses antibodies to the microorganism as the specific binding pair member on

4 the capture zone. Preferred dye reagents include Basic Blue 3, Basic Blue 16 and Rhodamine 6G.

DESCRIPTION OF THE PREFERRED EMBODIMENT

Figure 1:
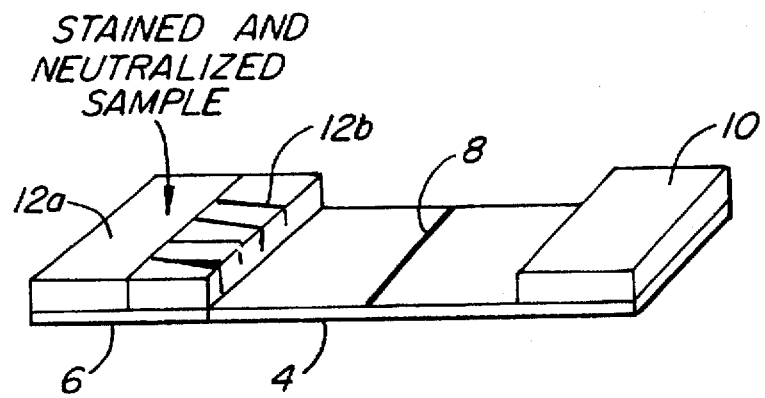
FIG. 1 illustrates a test article constructed in accordance with the principles of the present invention.

The present invention provides methods, devices and kits for detecting analytes in a fluid sample suspected of containing such analyte. More particularly, the present invention provides solid phase specific binding assays in which targeted microorganisms can be detected by direct staining of the microorganism. The direct staining of the microorganism provides a simple and convenient method for transforming the microorganism into a detectable species. The stained microorganisms are thereby rendered capable of detection by visual, spectrophotometric or fluorometric means when aggregated or accumulated in a capture zone as described in more detail hereafter.

Before proceeding further with the detailed description of the invention, a number of terms will be defined.

"Sample suspected of containing microorganism" shall mean any sample that is reasonably suspected of containing a microorganism can be analyzed by the method of the present invention. Such samples can include human, animal or man-made samples. The sample can be prepared in any convenient medium which does not interfere with the assay. Typically, the sample is an aqueous solution or biological fluid as described in more detail below.

The fluid sample may be a biological fluid such as, but not limited to, whole blood, serum, plasma, nasal secretions, sputum, urine, sweat, saliva, transdermal exudates, pharyngeal exudates, bronchoalveolar lavage, tracheal aspirations, cerebrospinal fluid, vaginal or urethral secretions, or the like. Herein, fluid homogenates of cellular tissues such as, for example, hair, skin and nail scrapings, meat extracts and skins of fruits and nuts are also considered biological fluids. Fluid samples also include nonbiological fluids such as, for example, soil extracts and water supplies. Multiple different organisms may be detected from a single fluid sample.

"Specific binding pair member" (sbp member) shall mean a molecule which is one of two different molecules, having an area on the surface or in a cavity which specifically binds to and is thereby defined as being complementary with a particular spatial and polar organization of the other molecule. The two molecules are related in the sense that their binding to each other is such that they are capable of distinguishing their binding partner from other assay constituents having similar characteristics. The members of the specific binding pair are referred to as ligand and receptor (antiligand), sbp member and sbp partner, and the like. Complementary sbp members bind to each other, as for example, a ligand and its complementary receptor. Sbp members will usually be members of an immunological binding pair such as an antigen-antibody, although other specific binding pairs, such as biotin-avidin, hormoneshormone receptors, nucleic acid duplexes, IgG-protein A, and the like are specific binding pairs which are not immunological binding pairs.

"Ligand" shall mean any organic compound for which a receptor naturally exists or can be prepared.

"Antigen" shall mean any compound capable of binding to an antibody, or against which antibodies can be raised.

"Receptor" shall mean any compound or composition capable of recognizing a particular spatial or polar orientation of a molecule, e.g., epitopic or determinant site. Illustrative receptors include: antibodies, enzymes, thyroxine binding globulin, intrinsic factor, lectins, nucleic acids, protein A, complement, complement Clq, and the like. Receptors are also referred to as antiligands.

"Antibody" shall mean an immunoglobulin having an area on its surface or in a cavity that specifically binds to and is thereby defined as complementary with a particular spatial and polar organization of another molecule. The antibody can be polyclonal or monoclonal. Antibodies may include a complete immunoglobulin or fragments thereof, which immunoglobulins include the various classes and isotypes, such as IgA (IgA1 and IgA2), IgD, IgE, IgM, and IgG (IgG1, IgG2, IgG3, and IgG4) etc. Fragments thereof may included Fab, Fv and F(ab')$_2$, Fab', and the like.

"Microorganism" shall mean a member of one of the following classes: bacteria, fungi, algae, protozoa or viruses.

"Ancillary materials" shall mean any materials frequently be employed in an assay in accordance with the present invention. For example, buffers will normally be present in the labelling means, the neutralization means, as well as stabilizers for the assay medium and assay components. Frequently, in addition to these additives, additional proteins, such as albumins, or surfactants, non-ionic or ionic, binding enhancers, e.g. polyalkylene glycols, or the like, may be present.

Generally, the devices and methods of the present invention of the present invention employ lateral flow assay techniques as generally described in U.S. Pat. Nos. 5,424,193, 4,943,522; 4,861,711; 4,857,453; 4,855,240; 4,775,636; 4,703,017; 4,361,537; 4,235,601; 4,168,146; 4,094,647; co-pending application U.S. Ser. No. 07/639,967, European Patent Application Nos. 451,800; 158,746; 276,152; 306,772 and British Patent Application No. 2,204,398; each of which is incorporated herein by reference.

Devices of the present invention generally include a labelling reagent comprising a dye for directly staining the microorganism; a neutralizing means to adjust the pH of the stained sample to a physiological pH; a matrix defining a flow path from a sample receiving zone to a capture zone located downstream from the sample receiving zone; and located in the capture zone an immobilized specific binding pair member for the microorganism being detected. Optionally, the device may also comprise a sample receiving pad in fluid contact with, and upstream of, the sample receiving zone.

Combination of the sample with the dye results in direct staining of the microorganism. Typically, this is done at an alkaline pH. By "alkaline pH" is meant a pH of at least about 10, preferably about 11 to 14, and more preferably about 13–14. The pH of the staining step will vary depending on the source and nature of the fluid sample, the microorganism being detected, the dye being used and other factors which will be apparent to one of skill in the art. The stained sample may be contacted directly with the matrix and allowed to flow to the capture zone wherein the stained microorganism will be captured by the sbp member. Preferably, subsequent to staining, the pH of the sample is adjusted to a physiological pH. By "physiological pH" is meant a pH which allows specific binding of the microorganism to a specific binding pair member for the microorganism. Typically, this will be a pH of about 5 to 9, preferably about 6 to 8. By "specific binding" is meant a binding similar to that of a molecule to its complementary specific binding pair member. The pH of the sample after neutralization will vary depending on the source and nature of the fluid sample, the microorganism being detected, the specific binding pair member in the capture zone, the dye being used and other factors which will be apparent to one of skill in the art.

The sample comprising the stained microorganism will flow from the sample receiving zone to the capture zone along the flow path defined by the matrix. Accumulation of the stained microorganism in the capture zone is based on the amount of microorganism that was present in the sample. The accumulation of the stained microorganism in the capture zone provides a means to detect and identify the presence of microorganism in the sample.

Typically, the labelling reagent comprises a dye capable of directly staining the microorganism. By "directly staining" is meant a process in which the dye associates directly with the microorganism as opposed to a process in which the dye first binds covalently or noncovalently to another molecule which subsequently binds to the microorganism. The dye may coat the surface of the microorganism, bind to surface antigens or receptors, intercalate into cellular membranes or enter the intracellular regions of the microorganism. Entry of dye into the intracellular region of the microorganism allows for the staining of soluble analytes contained within the microorganism.

The choice of dye is determined largely by the microorganism that is being detected. Preferably, the microorganism being detected will be specifically stained by the dye. However, such specific staining is not essential to the success of the assay because specificity of detection is also furnished by the specific binding pair member located on the capture zone. Numerous different microorganisms are known to be specifically stained by particular dyes. Mycobacterium and Nocardia are specifically stained by sequential treatment with carbolfuchsin (a mixture of Basic Fuchsin and phenol), acid-alcohol and Methylene Blue counterstains. Endospore staining of Clostridium bacilli is accomplished by Malachite Green. Eubacteria and cyanobacteria have cell walls surrounded by glycocalyx capsular membranes which are detected by staining with India ink. Certain intracellular constituents are also susceptible to specific staining. For example, poly β-hydroxybutyric acid, which is intracellularly stored in eukaryotes can be detected by staining with Sudan Black B. Similarly, staining of intracellular polyphosphate is used to distinguish *Corynebacterium diphtheriae* from similar species by staining with Toluidine Blue. Acridine Orange may be used to stain and detect intracellular DNA.

Typically, the dyes are polycyclic, condensed heteroaromatic organic compounds, preferably tricyclic compounds such as, for example, phenoxazines, phenazines, phenothiazines, acridines, fluoresceins and rhodamines. It is understood that the dyes are typically used in the form of salts provided as addition products of the organic dye with inorganic or organic acids or alkylating agents and that the salt forming moiety can vary widely within the spirit of the invention. The polycyclic nucleus may be substituted with a variety of substituents selected from the group consisting of alkyl, halo, hydroxy, alkoxy, sulfo, amino, monoalkylamino, dialkylamino, alkylazo and arylazo. The term "alkyl" refers to a branched or straight chain acyclic, monovalent saturated hydrocarbon radical of one to twenty carbon atoms. The term "aryl" refers to an optionally substituted aromatic monovalent carbocyclic radical having a single ring (e.g., phenyl) or more than one condensed ring (e.g., naphthyl, anthracenyl). The term "arylazo" refers to the group aryl-N=N—. Often the dyes carry nitrogen substituents on the polynuclear ring. Dyes containing nitrogen substituents such as amino, dialkylamino, such as, for example, dimethylamino and diethylamino, and substituted arylazo are particularly effective for staining and detecting fungal pathogens such as Candida.

The dye reagents of this invention find particular utility in the direct staining and detection of Candida. It has been discovered that certain dyes stain Candida cells under alkaline conditions and produce visible signal even after neutralization. These dyes include Basic Blue 3, N-[7-Dimethylamino-3H-phenoxazin-3-ylidene]-N-ethylethanaminium chloride (CI 51004, CAS 33203-82-6), Basic Blue 16, 7-Amino-2,8 dimethyl-3-[(hydroxynaphthyl) azo]-5-phenylphenazinium chloride, (Indoine Blue, CI 12210, CAS 4569-88-4) and Rhodamine 6G, N-[6-aminoethyl-9-(2-carbethoxyphenyl)-2,7-dimethyl-3H-xanthene-3-ylidene]ethanaminium chloride (Basic Red 1, CI 45160, CAS 989-38-8).

Yeast viability can be detected with the use of the fluorescent molecule FUN-1™ (Molecular Probes, Inc., Eugene, Oreg.) which binds to intact intracellular vacuoles that, in turn, form compact structures resulting in a shift to orange-red fluorescence in metabolically active yeast cells. Yeast cells can also be probed using membrane permeable derivatives of chloromethylcoumarin, e.g., 7-amino-chloromethylcoumarin (CellTracker™ Blue CMAC, Molecular Probes, Inc.) which stains intracellular vacuoles. Further, yeast cells can be stained using fluorescent probes which target binding sites in mitochondria. MitoTracker™ Green FM (Molecular Probes, Inc.) binds to accessible thiol moieties on peptides and proteins to yield an intense fluorescence when concentrated in the lipid environment of the mitochondrial membrane. Also SYTO™ 18 (Molecular Probes, Inc.) stains yeast cells by binding to mitochondrial nucleic acids.

Wheat germ agglutinin conjugated to various fluorescent molecules, e.g., Rhodamine B, fluorescein, tetramethyl rhodamine, BODIPY FL™ (Molecular Probes Inc.) can also serve as yeast cell labelling reagents by selectively binding to sialic acid and N-acetylglucosamine residues on the yeast cells.

Additional reagents and chemical cascades for staining microorganisms may involve tetrazolium salts as substrates for intracellular or surface oxidoreductases, e.g., alcohol dehydrogenase, when used alone or in conjunction with electron mediators such as phenazine methosulfate or cofactors, e.g., NAD(H) or FMN.

Microorganisms can also be stained by using esters of alpha- or beta-naphthols which react with microbial hydrolases, esterases or phosphatases to form colored complexes in the presence of diazonium salts when supplied simultaneously in the assay.

These dye reagents directly stain Candida cells making them the detector label. This obviates the need for the immunologically mediated binding of a label to he microorganism. The stained cells maintain their antigenicity, thus allowing their capture by a specific binding pair member immobilized in the capture zone. Furthermore, soluble analytes extracted from Candida cells also produce visible signal. Thus, the methods of detection provided by this invention are not limited to whole cell detection.

Generally, the sample is combined with the dye reagent at an alkaline pH under conditions which facilitate the staining of the organism. The dye reagent is typically in sodium or potassium hydroxide and is weakly buffered to allow for subsequent neutralization. The particular buffer employed is not critical to the present invention but in individual assays, or with particular dyes or microorganisms, a particular buffer may be preferred over another. Typically, the dye reagent is provided as a wholly aqueous solution. However certain dyes may be provided in a mixed organic/aqueous medium. The organic component may be a water miscible solvent such as an alcohol, ether and the like. The dye-sample mixture may be incubated for a period of about 1 to 30 minutes, preferably 1 to 10 minutes and more preferably about 1 to 2 minutes prior to neutralization. The dye-sample mixture may be agitated, vortexed, mixed, swirled or sonicated to improve the efficiency of staining. The incubation at room temperature is preferred. However certain stains and organisms may require heating to facilitate the direct staining of the organism. Generally the sample will be present on a swab, wooden spatula, or other form of collection device. Specialized extraction devices for expressing sample collected on such collection devices are well known to those skilled in the art and can be used in conduction with the present invention.

A wide range of microorganisms may be stained and detected by the methods provided by this invention. Microorganisms detectable by the methods of the present invention generally include bacteria and fungi. Such microorganism include, but are not limited to Staphylococcus aureus, Streptococcus Group A and B, *Escherichia coli, Legionella pneumophilia, Pneumocystis carinii, Neisseria meningitidis, Neisseria gonorrheae, Gardnerella vaginalis, Proteus vulgaris, Helicobacter pylori, Chlamydia, Trichomonas vaginalis, Toxoplasmosis, Haemophilus influenzae* species, Cryptococcus and Candida. The methods of this invention find particular utility in directly staining and detecting fungal pathogens such as Candida and Aspergillus. Though not intending to be bound by any one particular theory, the fungal cell walls contain relatively high proportions of mannan-based oligosaccharides and are particularly resistant to degradation under alkaline conditions. Thus it is believed that fungi are more capable of retaining antigenicity after the staining and neutralization procedures.

The dye-sample mixture is usually neutralized prior to capture of the stained microorganism at the capture zone. Generally, neutralization involves adjusting the pH of the stained sample to a physiological pH. Neutralization is generally necessary for effective capture of the microorganism on the capture zone. Optionally, cellular matter may be separated prior to neutralization. It has been surprisingly discovered that stained Candida species retain visible dye after neutralization. Neutralization may be accomplished prior to addition of the sample to the sample receiving pad or the sample receiving zone. Alternatively, the neutralizing means may be located in the sample receiving pad. Neutralization may be accomplished by any convenient method. Typically, the reagent used for neutralization comprises an acid of sufficient buffering capacity to reduce the pH of the stained sample to a physiological pH. Ideally, this pH will be such that the specific binding pair member on the capture zone will be able to specifically bind to and immobilize the stained microorganism on the capture zone. Since the capture of stained microorganism will typically employ a biological binding interaction, it is important that the pH of the neutralized sample be in a range that permits such a binding to occur. For example, when the binding interaction is an antigen-antibody interaction such as when the specific binding pair member on the capture zone is an antibody against the microorganism, the pH of the neutralized sample will typically be in the range of about 5 to 8, preferably about 6 to 8. The appropriate pH for other binding interactions such as, for example, lectin-glycoprotein binding and ligand-cell surface receptor binding is known to or readily ascertainable by those skilled in the art. This results in accumulation of the microorganism in the capture zone and generation of a detectable signal.

Any appropriate buffer, such as for example phosphate, citrate, acetate and the like may be employed to neutralize the stained sample. Typically, a neutralization reagent of high buffering capacity is provided by using a polyacid, preferably a polycarboxylic acid. The acid should be capable of mixing freely with the sample. Preferably, it will be water-soluble and if provided as a solid, dissolve rapidly in the sample. Alternatively, the acid may be provided in liquid form, e.g., buffered HCl. In this latter situation rapid dissolution is not critical; however the acid should be freely miscible with the sample such that neutralization can occur rapidly. The acid may also be a solid phase resin such as a Dowex™ resin.

The pH of the neutralized sample is controlled by the initial pH and buffer capacity of the dye reagent-sample mixture, and the $pK_a$, buffer capacity and quantity used of the neutralizing means. A variety of different acids may be used. Carboxylic acids such as oxalic acid, malonic acid, dihydroxymalonic acid, glutaric acid, succinic acid, citric acid, tartaric acid, glycolic acid, glyoxylic acid, maleic acid etc. and the like may be used. Polycarboxylic acids are generally preferred. The neutralization reagent may also be a combination of acids. Typically, an appropriate amount, readily determinable by one of skill in the art, of an acid or combination of acids with a $pK_a$ of between 2 and 5 will provide adequate buffering capacity to bring the pH of the sample to a point where capture of the stained microorganism by the specific binding pair member can occur. The neutralization reagent may be impregnated in the sample receiving pad. As used hereinafter, "impregnated" is meant to refer to a state of permeation or reversible surface adherence. Substances which are impregnated are not immobilized within or upon the support matrix, but are capable of being mixed or suspended in fluids placed on the support matrix. Alternatively, the neutralization reagent may be immobilized on the sample receiving pad.

The sample receiving pad is in fluid contact with the support matrix pad and allows transfer of the sample to the sample receiving zone in a controlled manner. The sample receiving pad is generally composed of a non-bibulous material. Frequently, the sample receiving pad comprises two pads; a first pad to which the sample is applied and a second pad which is inverted relative to the first pad and in fluid contact with the membrane containing the capture zone. In a preferred embodiment of the invention, the backing of the second segment is face up. Thus the second pad acts as a bridge in transferring the sample to the membrane comprising the capture zone. This split configuration of the sample receiving pad creates an interface between the sample receiving pad and the membrane. The dye is generally a colloid and the membrane is able to trap the large crystalline dye structures. Thereby excess dye accumulates at this membrane interface which thus acts as a prefilter and reduces background, whereas dye colloids bound to the antigen flow through the membrane.

The support matrix of the device may be capable of non-bibulous lateral flow. By "non-bibulous lateral flow" is meant liquid flow in which all of the dissolved or dispersed components of the liquid are carried at substantially equal rates and with relatively unimpaired flow laterally through the membrane, as opposed to preferential retention of one or more components as would occur, e.g., in materials capable of adsorbing or imbibing one or more components.

A typical non-bibulous material suitable for use as a support matrix is high density polyethylene sheet material manufactured by Porex Technologies Corp. of Fairburn, Ga., USA. The sheet material has an open pore structure with a typical density, at 40% void volume, of 0.57 gm/cc and an average pore diameter of 1 to 250 micrometers, the average generally being from 3 to 100 micrometers. The optimum pore diameter for the membrane for use in the invention is about 10 to about 50 µm. The membranes typically are from about 1 mil to about 15 mils in thickness, typically in the range of from 5 or 10 mils, but may be up to 200 mils and thicker. The membrane may be backed by a generally water impervious layer, such as mylar. When employed, the backing is generally fastened to the membrane by an adhesive, such as 3M 444 double-sided adhesive tape. Typically, a water impervious backing is used for membranes of low thickness. A wide variety of polymers may be used provided that they do not bind nonspecifically to the assay components and do not interfere with flow of the sample. Illustrative polymers include polyethylene, polypropylene, polystyrene and the like. Alternatively, the membrane may be self supporting. Other non-bibulous membranes, such as polyvinyl chloride, polyvinyl acetate, copolymers of vinyl acetate and vinyl chloride, polyamide, polycarbonate, polystyrene, and the like, can also be used.

Bibulous materials, such as untreated paper, cellulose blends, nitrocellulose, polyester, an acrylonitrile copolymer, rayon, glass fiber, and the like may also be employed as support matrix materials to provide either bibulous or non-bibulous flow. Especially preferred are microporous materials made from nitrocellulose, by which term is meant any nitric acid ester of cellulose. Thus suitable materials may include nitrocellulose in combination with carboxylic acid esters of cellulose. The pore size of nitrocellulose membranes may vary widely, but is preferably within 5 to 20 microns, preferably 8 to 15 microns. To provide non-bibulous flow, these materials may be treated with blocking agents that may block the forces which account for the bibulous nature of bibulous membranes. Suitable blocking agents include bovine serum albumin, methylated bovine serum albumin, whole animal serum, casein, and non-fat dry milk.

Typically, the support matrix will define a flow path. The flow path is generally axial, although other configurations are acceptable and may be preferred for some embodiments. For example, radial or circular flow paths are particularly useful for test devices which can simultaneously detect the presence of multiple analytes in a sample such as when identifying which one of a particular Candida species, such as, for example, *C. albicans, C. glabrata, C. tropicalis, C. parapsilosis, C. krusei* and *C. guillemondii*. Alternatively, such a flow path is also useful for simultaneously identifying the presence of microorganisms of different species, such as *C. albicans* and *Trichomonas vaginalis*. Radial flow paths combined with lateral flow are disclosed in U.S. Pat. No. 4,943,522, incorporated herein by reference. Circular flow paths combined with lateral flow are disclosed in published British application GB 2,239,313, incorporated herein by reference.

The support matrix will often be divided into different zones: the sample receiving zone and the capture zone. The support matrix may be composed of different membranes in the different zones of a single device. For example, zones of different porosity may be desired to provide a filtering function in the sample receiving zone and non-bibulous flow in the downstream zones. Other combinations may be desired for particular uses.

The sample receiving zone provides a means for applying the sample to the devices of the present invention. In some embodiments, the sample receiving zone will have a low analyte retention rate. Treatment of the sample receiving zone to immobilize a protein-blocking reagent on the surface will typically provide low retention properties. This treatment also provides increased wetability and wicking action to speed the downstream flow of the sample. The sample receiving zone may also serve as a means for filtering particulates from the sample.

The support matrix also contains a capture zone. The sample receiving zone is in fluid contact with the membrane comprising the capture zone. A specific binding pair member for the microorganism is immobilized in the capture zone. Typically, the specific binding pair member is an anti-microorganism immunoglobulin. Alternatively, the specific binding pair member may be a ligand for a receptor on the cell surface of the microorganism, such as a lectin which specifically binds to a cell surface glycoprotein. When soluble analytes are being detected the specific binding pair member may be an antibody to the analyte or any other species which specifically binds to the analyte. For example, if intracellular DNA is being detected, the specific binding pair member may be a complementary strand of DNA. Either monoclonal antibodies or antigen-specific polyclonal antibodies may be employed. Antibodies specific to many different microorganisms are either known to, or may be prepared by, those skilled in the art. For example, specific antibodies exist for microorganisms such as, *Legionella pneumophila, Pneumocystis carinii, Haemophilus influenzae B, Neisseria meningitidis, Streptococcus pyogenes*, Cryptococcus, and Candida, *Textbook of Diagnostic Microbiology*, Mahon and Manaselis (W. B. Saunders and Co., 1995). Alternatively, persons of skill may readily prepare antibodies to analytes of interest by methods well known in the art. See, e.g., Harlow and Lane, "Antibodies, A Laboratory Manual", Cold Spring Harbor Laboratory, Cold Spring Harbor N.Y. (1988), incorporated herein by reference.

The matrix may have to be activated in order to immobilize the specific binding pair member. Various methods may be employed based on the nature of the membrane and the particular binding pair member being employed. Generally when the membrane is nitrocellulose or a mixed nitrocellulose ester no special chemical linkage is required. For other materials, various other techniques such as activation by carbonyldiimidazole, glutaraldehyde, succinic acid, cyanogen bromide and the like may be employed. Alternatively, particles having an immobilized specific binding pair member may be used to immobilize the specific binding pair member on the capture zone. Exemplary of such particles are latex beads made of polystyrene, polyacrylates and polyacrylamides. The particles must be capable of nondiffusive attachment of the specific binding pair member by covalent or noncovalent binding. When the specific binding pair member is to be covalently bound a variety of particles containing functionalities such as carboxylic acids, aldehydes, amines, maleiimides, thiols, hydroxyls and the like may be used. The particles may be applied to the capture zone by a standard printing process including the use of electrostatic and laser controlled jets, and printing probe or type face. Alternatively, a suspension of the particles can be transferred to the capture zone by inscribing with a pen or microcapillary tube.

A bibulous absorbent zone is generally included in the devices of the present invention. The absorbent zone is located downstream from the capture zone. The absorbent zone is a means for removing excess sample and free dye or stained species other than the analyte of interest from the matrix of the device. Generally, the absorbent zone will consist of an absorbent material such as filter paper, a glass fiber filter, or the like.

The device may contain an end of assay indicator. The end of assay indicator may consist of a pH indicating reagent (such as bromocresol green) impregnated in the absorbent zone. Upon contact with the treated sample, a pH change occurs in the processed absorbent. This pH shift converts the pH indicator to a different color (for instance, bromocresol green may be converted from yellow to blue) which is seen in an observation window over the absorbent zone. This technology may also serve as an internal assay control. For example, a neutralized stained sample will convert the end of assay indicator from bright yellow to blue. If the neutralization is incomplete, the lower pH of the acidic sample solution will produce a green end color. An underneutralized sample may produce suspect results, the wrong color (green in this case) in the end of assay vent can serve as a signal that the assay may be comprised.

Alternatively, the end of assay may be constructed by applying a line of soluble ink on the capture zone (at the interface with the absorbent zone). The liquid front moving through the capture zone will solubilize the ink and transfer it into the absorbent. The resulting color change will be seen in an observation window above the absorbent zone, signifying end of assay.

In some embodiments of the present invention, multiple microorganisms may be simultaneously detected from a single sample. Generally, a plurality of capture zones is located downstream of the sample receiving zone. Each capture zone detects a different microorganism in the sample by virtue of having immobilized therein a specific binding pair member for a different microorganism. For example, each of the capture zones may have a different specific binding pair member, such as an antibody, which binds specifically to a different species of Candida, thus allowing detection and discrimination between different species of Candida. Alternatively, each of the capture zones may have a different genus specific, specific binding pair member for different genuses of microorganisms. For example, a device containing two capture zones, one with an antibody against Candida, and the other with an antibody against *Trichomonas vaginalis*, allows one to specifically identify a microorganism in a sample as Candida or *Trichomonas vaginalis*, respectively. It is also possible to determine, by immobilizing a plurality of different specific binding pair members for a plurality of different microorganisms on a single capture zone, whether the sample contains any one of those organisms. For example, immobilizing a cocktail of antibodies, each raised specifically against a particular Candida species, or each raised specifically against a particular genus of microorganism, on a single capture zone, allows one to determine whether any one of those particular Candida species, or any one of those particular microorganisms is present in the sample. Alternatively, instead of using a mixture of antibodies, one may immobilize a single antibody which crossreacts with all of the microorganisms to be detected.

Using a single dye to stain the plurality of microorganisms is preferred. However one may also use a mixture of different dyes to optimize the staining of the plurality of microorganisms.

Devices which simultaneously detect many different analytes have a variety of uses. For example, sputum samples of patients having respiratory infections may be evaluated for the presence of a variety of pathogens including *Mycoplasma pneumoniae, Legionella pneumophila, Streptococcus pneumoniae, Hemophilus influenzae,* and *Moraxella catarrhalis*. Genital discharges may be assessed for the presence of *Chlamydia trachomatis, Neisseria gonorrhoeae, Mycoplasma pneumonia, Ureaplasma urealyticum,* and *Gardnerella vaginalis*. Thus, accurate diagnosis of common clinical syndromes may be rapidly obtained in an outpatient setting, even in mixed infections as frequently encountered in urethritis or vaginitis.

Another embodiment of this invention provides non-lateral flow assays for determining the presence of a microorganism in a sample. The assay comprises a means for labelling the microorganism to form a labelled microorganism and capturing the labelled microorganism on a matrix comprising a capture zone on which is immobilized a specific binding pair member for the microorganism, wherein said labelling means comprises:

1) combining the sample with a dye reagent which directly stains the microorganism to provide a stained sample comprising a stained microorganism, and 2) neutralizing the stained sample prior to capturing the stained microorganism on the capture zone; and relating the accumulation of the stained microorganism in the capture zone to the presence or absence of the microorganism in the sample.

Solid phase separation assays are disclosed in U.S. Pat. No. 5,308,775, incorporated herein by reference, in which analytes are captured on a solid phase by a first sbp member and a labelled second sbp member for the analyte is used to detect the binding of the analyte to the solid phase. Enzymes, fluorescers and dye sols are used as labels. The present invention obviates the need to use a labelled second sbp member by directly staining the analyte, i.e. the microorganism and thus provides a more direct method of detection.

Assays of this type are generally non-lateral flow membrane assays. In this type of assay, a specific binding pair member for the microorganism is immobilized on the capture zone on the membrane. The stained and neutralized sample is contacted with the capture zone. Microorganism present in the sample binds to its specific binding pair member located on the capture zone, while the remaining sample flows through the membrane. Accumulation of the stained microorganism on the capture zone may then be related to the presence of microorganism present in the sample.

The accumulation of stained microorganism may be assessed either visually or by optical detection devices, such as reflectance analyzers, video image analyzers and the like. The accumulation of stained microorganism can be assessed either to determine its presence or absence of in the capture zone or the visible intensity of accumulated stained microorganism which may by correlated with the concentration of microorganism in the biological sample. The correlation between the visible intensity of accumulated stained microorganism and microorganism concentration in the sample may be made by comparison of the visible intensity to a reference standard. Optical detection devices may be programmed to automatically perform this comparison by means similar to that used by the Quidel Reflective Analyzer, Catalog No. QU0801 (Quidel Corp., San Diego, Calif.). Visual comparison is also possible by visual evaluation of the intensity and a color key such as used in the Quidel Total IgE Test Catalog No. 0701 (a multi-step ELISA assay). Video image analyzers for performing this function are also known to those of skill in the art (*Immunocytochemistry: A Practical Approach*, ed. J. E. Beasely, IRL Press, (1993)). Typically, a video image analyzer comprises a digitizing tablet linked to a host computer. The matrix and capture zone are inspected by a microscope or other scanning device and the microscopic image is projected onto the digitizing tablet by a video camera. The computer analyzes the X,Y coordinates of the image to produce a digitized image. Such means are useful for performing high throughput automated screening of multiple samples. Thus, analyte concentration may be determined by the present invention.

If the dye used is a visible dye then the microorganism is visually discernible. Alternatively, if a fluorescent dye is used the accumulation of the microorganism can be detected by employing a simple fluorescent detection means such as, for example, a hand held ultraviolet lamp (Mineralight lamp, UVP Inc., San Gabriel Calif.) or a fluorescent microscope. Thus, a variety of detection methods are available to detect the accumulated stained microorganism on the capture zone.

Referring now to FIG. 1, a test article 2 constructed in accordance with the principles of the present invention is illustrated. The test article 2 will employ a non-bibulous support matrix 4 and a lateral flow format. Persons of skill will appreciate that other devices employing different assay formats, bibulous support matrixes, and other modifications may be constructed for use with the labelling means of the present invention to directly stain and detect microorganisms.

The support matrix 4 is capable of receiving fluid samples and conducting the samples in a lateral direction. The support matrix 4 is divided into two zones: a sample receiving zone 6, and a capture zone 8. An absorbent zone 10 which contacts the support matrix 4 is present downstream of the capture zone. The absorbent zone 10 is constructed of a material which can absorb the fluid sample. A sample receiving pad 12, comprising two segments 12a and 12b, is located on and in fluid contact with the sample receiving zone. Segments 12a and 12b are inverted with respect to each other, i.e, the backing of segment 12b is face up.

The stained and neutralized sample is applied to the sample receiving pad segment 12a. The fluid sample flows through segment 12b into the sample receiving zone and flows laterally to the capture zone 8. The inverted sample pad 12b, which may contain neutralizer, acts as a bridge between the sample receiving pad segment and the membrane. Free dye accumulates at the interface between the inverted segment 12b and the support matrix. The capture zone 8 has an immobilized specific binding pair member for the microorganism being detected. The stained microorganism in the sample binds to the specific binding pair member in the capture zone 8 and is immobilized therein. Excess fluid, free dye, other microorganisms and the like continue lateral flow through the capture zone 8 into the absorbent zone 10. Microorganism present in the fluid sample is detected by observing the accumulation of color from the stained microorganisms in the capture zone 8.

Figure 2:
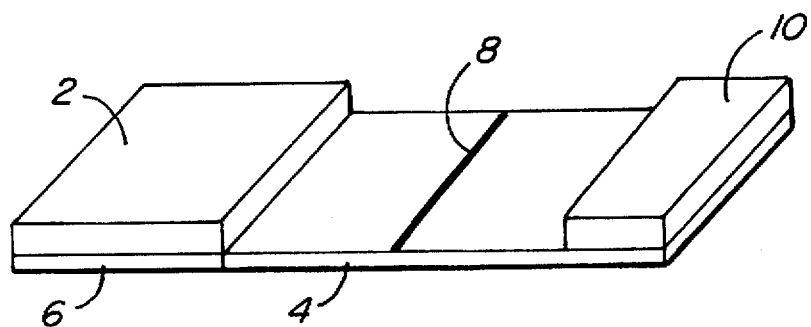
FIG. 2 illustrates a test article constructed in accordance with the principles of the present invention wherein the neutralizing means is located in the sample receiving pad.

With reference now to FIG. 2, a test article 2 constructed in accordance with the principles of the present invention is illustrated. This test article is similar to that shown in FIG. 1, but contains a sample receiving pad 2 in which the neutralizing means is impregnated. The sample receiving pad is located on and in fluid contact with the sample receiving zone 6 of the support matrix 4. The stained sample is applied to the sample receiving pad 2 and is neutralized. The neutralized sample flows laterally along the support matrix 4 to the capture zone 8. The capture zone 8 has an immobilized specific binding pair member for the microorganism being detected. The stained microorganism in the sample binds to the specific binding pair member in the capture zone 8 and is immobilized therein. Excess fluid, free dye, other microorganisms and the like continue lateral flow through the capture zone 8 into the absorbent zone 10. Microorganism present in the fluid sample is detected by observing the accumulation of color from the stained microorganisms in the capture zone 8.

Figure 3:
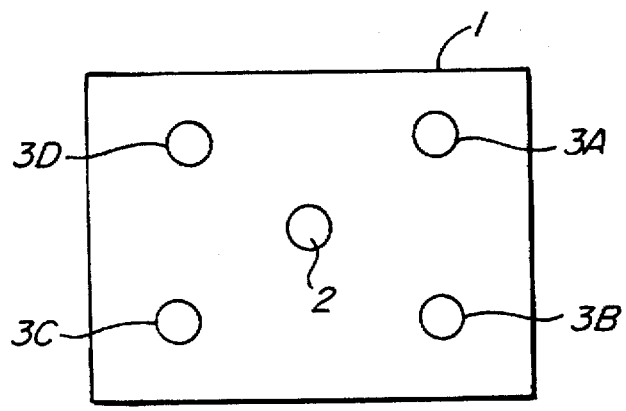
FIG. 3 illustrates a test article constructed in accordance with the principles of the present invention for simultaneously determining the presence of at least one of four different analytes.

FIG. 3 illustrates a device for the simultaneous detection of different microorganisms or different species of a particular genus of microorganism. This embodiment of the present invention is particularly useful for the detection of pathogens which are commonly assayed as a group such as when a bacterial infection is suspected and one desires to identify the specific bacterium and begin the appropriate therapeutic regimen.

The device comprises a matrix 1 having a sample receiving zone 2 and four capture zones 3A–D. The matrix 1 provides lateral flow of stained and neutralized fluid samples placed on the centrally positioned sample receiving zone 2. The fluid sample flows laterally in a radial fashion into each capture zone 4A–D.

Each capture zone 4A–D contains a different specific binding pair member immobilized on the surface of the matrix 1. Each binding pair member binds to a different microorganism. When the stained fluid reaches the capture zones 4A–D, microorganisms specific the immobilized specific binding pair members are retained. The presence of specific microorganisms is thus simultaneously determined by observing color changes in the capture zones 4A–D.

The following examples are offered by way of illustration, not by way of limitation.

EXAMPLES

Abbreviations

BSA—Bovine serum albumin
PBS—Phosphate buffered saline
DEAE—Diethylaminoethyl

1. Identification of Candida cells using Basic Blue 3

Basic Blue 3 dye (Sigma, St. Louis, Mo.) was dissolved at concentration of 0.1–1.0 mg/mL (0.3–3 mM) in an aqueous solution of 0.2M sodium hydroxide, 2.5 g/L sodium polyphosphate, pH≦13. The color of the solution is allowed to shift from blue to purple prior to use (1–2 hours)

A vaginal swab containing Candida cells is placed in a pliable plastic tube containing 0.5 mL of dye solution and swirled or vortexed for at least 10 seconds. The swab remains in the dye solution for at least one minute.

The solution is neutralized with 0.05M citric acid to pH 7–8. The swab is then expressed by squeezing the tube and the swab is then discarded.

0.1 mL of neutralized sample is applied to the assay device which consists of a sample receiving pad in fluid contact with a sample receiving zone of a matrix comprising a sample receiving zone, a capture zone and a absorbent pad as shown in FIGS. 1 and 2. Preparation of the sample receiving pads and capture zones are prepared by methods similar to those disclosed in U.S. Pat. No. 5,424,193, incorporated herein by reference.

(a) a sample receiving pad is made of mylar backed acrylic weave (New Merge, DuPont, Wilmington, Del.), treated with methylated BSA in 50 mM Tris-HCl, pH 8.0.

(b) a second inverted New Merge pad similarly treated with methylated BSA in Tris-HCl, pH 8.0 bridges the sample receiving pad from (a) and the nitrocellulose membrane containing the capture zone described in (c).

(c) a strip of supported or unsupported nitrocellulose (Schleicher and Schuell) with a dried line of DEAE purified rabbit anti-Candida antibody (Centers for Disease Control, Atlanta, Ga.) applied as follows: DEAE-purified rabbit anti-Candida, 1–2 mg/ml, was loaded into a pen and spotted on a line on nitrocellulose (8–15 micron pore size, Schleicher and Schuell) using a SE 780 X-Y plotter (Asea Brown Boveri) with a pen speed of 0.5 sec/cm. After air drying for 10 min., the spotted nitrocellulose was dipped into 10 mg/ml methylated BSA in 50 mM Tris-HCl, pH 8.0 and incubated submerged for 15 min. to block the remainder of the nitrocellulose. Next, it was blotted dry between two pieces of blotter absorbent (ED 939, Ahlstrom) for 5 min., then dried at 45° C. for 10 min. in a forced air oven. Optionally, the dried nitrocellulose was backed with a mylar sheet coated with double-stick adhesive tape (444,3M). It was stored in a dry room at 13% relative humidity.

(d) an absorbent cellulose wicking pad (Ahlstrom) is attached to the downstream end of the nitrocellulose membrane at the distal end from the sample receiving pad.

The sample was applied to the first New Merge pad (a) and allowed to wick onto and through the nitrocellulose membrane.

Signal was observed at the capture antibody zone as a purple colored line, usually appearing within 1–3 minutes, depending on the Candida concentration. Analytical sensitivity of 5000 cells/assay was achieved.

When swabs spotted with a phosphate buffered saline without Candida cells were used as a procedural control no purple line was observed at the antibody capture zone after 20 minutes.

2. Identification of Candida cells using Rhodamine 6G

The procedure of Example 2 was followed except that Rhodamine 6G was used in place of Basic Blue 3. A light red signal line was formed at the antibody capture zone. No signal was produced with the PBS control swab.

3. Identification of Streptococcus A cells using Basic Blue 3

Basic Blue 3 dye solution was prepared as in Example 1. Group A Streptococcus cells were placed in the stain solution for 1 minute. The cells were pelleted by centrifugation, supernatant discarded and the cells resuspended in PBS.

A reaction device was prepared as in Example 1, except that a 8 micron nitrocellulose membrane was used and rabbit anti-Group A Streptococcus was immobilized by drying onto the capture zone.

Positive signal developed on the capture zone as a purple line. A procedural negative control PBS swab did not produce color at the capture zone.

4. Specificity of detection for Candida

The same device as described in Example 1 was used. However, separate swabs are loaded with non Candida bacterial species at the following amounts and tested. *Gardnerella vaginalis* ATCC 14018, *Staphylococcus aureus* ATCC 25178, Group B Streptococcus type III, CDC 462, *Proteus vulgaris* ATCC 3315, each at $2.7 \times 10^6$ cells per assay and *Trichomonas vaginalis* at $2.7 \times 10^4$ cells/assay.

No signal was observed at the capture zone for any of the above species.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. An assay for determining the presence or absence of a microorganism in a fluid sample suspected of containing a microorganism, said assay comprising:
   a) combining the sample with a labeling reagent to form a labeled microorganism, said labeling reagent comprising a dye which directly stains the microorganism to provide a stained sample comprising a stained microorganism,
   b) contacting the stained sample with a matrix defining a flow path from a sample receiving zone to a capture zone located downstream from the sample receiving zone wherein said capture zone comprises an immobilized specific binding pair member for the microorganism, and
   c) observing the accumulation of the stained microorganism within the capture zone as a result of the stained microorganism flowing into and being immobilized within the capture zone by the specific binding pair member.

2. The assay as in claim 1, which further comprises combining the stained sample with a means for neutralization which adjusts the pH of the stained sample to a physiological pH prior to capture of the stained microorganism on the capture zone.

3. The assay as in claim 1, wherein the fluid is whole blood, serum or plasma.

4. The assay as in claim 2, wherein the sample is applied to the sample receiving zone.

5. The assay as in claim 2, wherein the means for neutralization is located in a sample receiving pad in fluid contact with and on the surface of the sample receiving zone.

6. The assay as in claim 2, wherein the means for neutralization is an acid with a pKa in the range of 2–5.

7. The assay as in claim 2, wherein the means for neutralization is a polycarboxylic acid.

8. The assay as in claim 7, wherein the polycarboxylic acid is selected from the group consisting of citric acid, succinic acid, malonic acid and tartaric acid.

9. The assay as in claim 2, wherein the specific binding pair member for the organism is an antibody to the microorganism.

10. The assay as in claim 9, wherein the antibody is a monoclonal antibody.

11. The assay as in claim 10, wherein the antibody is a polyclonal antibody.

12. The assay as in claim 1, wherein the specific binding pair member for the microorganism is a ligand to a cell surface receptor on the microorganism.

13. The assay as in claim 12, wherein the ligand is an antibody.

14. The assay as in claim 1, wherein the microorganism is a microbial pathogen.

15. The assay as in claim 14, wherein the pathogen is a Candida species.

16. The assay as in claim 14, wherein the pathogen is a bacterium.

17. The assay as in claim 16, wherein the bacterium is a gram-positive bacterium.

18. The assay as in claim 1, wherein the flow path defined by the sample receiving zone and the capture zone is lateral.

19. The assay as in claim 1, wherein the flow path defined by the sample receiving zone and the capture zone is vertical.

20. The assay as in claim 18, wherein the matrix is a bibulous flow membrane.

21. The assay as in claim 20, wherein the matrix is a fabric composed of a polyester, an acrylonitrile copolymer, rayon, glass fiber, cellulose, nitrocellulose, and blends thereof.

22. The assay as in claim 21, wherein the matrix has been treated with a blocking agent to render it non-bibulous.

23. The assay as in claim 22, wherein the blocking agent is methylated BSA.

24. The assay as in claim 18, wherein the matrix is a non-bibulous flow membrane.

25. The assay as in claim 1, wherein the dye is selected from the group consisting of substituted phenoxazines, phenazines, phenothiazines, acridines and fluoresceins and salts thereof.

26. The assay as in claim 25, wherein the phenoxazines, phenazines, phenothiazines, acridines and fluoresceins carry at least one substituent selected from the group consisting of amino, monoalkyl amino, dialkylamino and substituted arylazo.

27. The assay as in claim 26, wherein the dye is selected from the group consisting of Basic Blue 3, Basic Blue 16 and Rhodamine 6G.

28. The assay as in claim 1, wherein the microorganism is a Candida species.

29. The assay as in claim 27, wherein the microorganism is a Candida species.

30. An assay for determining the presence or absence of a microorganism in a fluid sample suspected of containing a microorganism, said assay comprising a means for labelling the microorganism to form a labelled microorganism, and capturing the labelled microorganism on a matrix comprising a capture zone on which is immobilized a specific binding pair member for said microorganism, wherein said labelling means comprises:
   1) combining the sample with a dye reagent which directly stains the microorganism to provide a stained sample comprising a stained microorganism, and
   2) neutralizing the stained sample to a physiological pH prior to capturing the stained microorganism on the capture zone; and relating the accumulation of the stained microorganism in the capture zone to the presence or absence of the microorganism in the sample.

31. The assay of claim 30, wherein the microorganism is a species of Candida.

32. The assay of claim 31, wherein the dye is selected from the group consisting of Basic Blue 3, Basic Blue 16 and Rhodamine 6G.

33. In an assay for determining the presence or absence of a microorganism in a fluid sample suspected of containing a microorganism, said assay comprising a means for labelling the microorganism to form a labelled microorganism, and capturing the labelled microorganism on a matrix comprising a capture zone on which is immobilized a specific binding pair member for said microorganism, the improvement comprising a labelling means which comprises:

1) combining the sample with a dye reagent which directly stains the microorganism to provide a stained sample comprising a stained microorganism, and 2) neutralizing the stained sample to a physiological pH prior to capturing the stained microorganism on the capture zone; and relating the accumulation of the stained microorganism in the capture zone to the presence or absence of the microorganism in the sample.

34. An assay for determining the presence or absence of at least one of a plurality of microorganisms in a fluid sample suspected of containing at least one of said microorganisms, said assay comprising:

a) combining the sample with a labelling reagent to provide a plurality of labelled microorganisms, said labelling reagent comprising a dye or mixture of dyes which directly stain the microorganisms to provide a stained sample comprising a plurality of stained microorganisms, b) optionally combining the stained sample with a neutralization reagent which adjusts the pH of the stained sample to a physiological pH to provide a neutralized sample, c) contacting the stained or neutralized sample with a matrix defining a flow path from a sample receiving zone to a plurality of capture zones located downstream from the sample receiving zone wherein each of said capture zones comprise an immobilized specific binding pair member each of which binds to a different microorganism, d) observing the accumulation of the stained microorganisms within the plurality of capture zones as a result of the stained microorganisms flowing into and being immobilized within the plurality of capture zones by each of the specific binding pair members, and e) relating the accumulation of stained microorganisms within the capture zones to the presence or absence of microorganism in the fluid sample.

35. The method of claim 34, wherein the labelling reagent comprises a single dye.

36. The method of claim 35, wherein the microorganisms are selected from the group consisting of Candida, Streptococcus, Trichomonas and Staphylococcus.

37. The method of claim 35, wherein the microorganisms are selected from the group consisting of *Candida albicans, Candida glabrata, Candida tropicalis, Candida parapsilosis* and *Candida guillemondii*.

38. A kit for detecting the presence of a microorganism in a fluid sample suspected of containing the microorganism, comprising in packaged combination:

(a) a dye reagent capable of directly staining the microorganism, and (b) a matrix defining a flow path from a sample receiving zone to a capture zone located downstream from the sample receiving zone, wherein the capture zone comprises an immobilized specific binding pair member for the microorganism.

* * * * *